United States Patent
Goldfine et al.

(10) Patent No.: US 7,280,940 B2
(45) Date of Patent: Oct. 9, 2007

(54) SEGMENTED FIELD DIELECTRIC SENSOR ARRAY FOR MATERIAL CHARACTERIZATION

(75) Inventors: Neil J. Goldfine, Newton, MA (US); Darrell E. Schlicker, Watertown, MA (US); Yanko K Sheiretov, Waltham, MA (US); Andrew P. Washabaugh, Chula Vista, CA (US); David C. Grundy, Reading, MA (US); Vladimir A. Zilberstein, Chestnut Hill, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 0 days.

(21) Appl. No.: 11/371,315

(22) Filed: Mar. 7, 2006

(65) Prior Publication Data

US 2006/0247896 A1 Nov. 2, 2006

Related U.S. Application Data

(60) Provisional application No. 60/659,266, filed on Mar. 7, 2005.

(51) Int. Cl.
*G06F 15/00* (2006.01)
(52) U.S. Cl. ...................................... 702/183
(58) Field of Classification Search ............... 702/182, 702/183, 116, 35, 34; 324/235, 238, 239, 324/240, 242, 237
See application file for complete search history.

(56) References Cited

U.S. PATENT DOCUMENTS

| | | | |
|---|---|---|---|
| 4,423,371 | A | 12/1983 | Senturia et al. |
| 4,814,690 | A | 3/1989 | Melcher et al. |
| 6,377,039 | B1 | 4/2002 | Goldfine et al. |
| 6,380,747 | B1 | 4/2002 | Goldfine et al. |
| 6,486,673 | B1 | 11/2002 | Goldfine et al. |
| 6,727,691 | B2 | 4/2004 | Goldfine et al. |
| 6,781,387 | B2 | 8/2004 | Goldfine et al. |
| 2002/0075006 | A1 | 6/2002 | Goldfine et al. |
| 2004/0056654 | A1* | 3/2004 | Goldfine et al. ............ 324/239 |
| 2004/0124834 | A1 | 7/2004 | Goldfine et al. |

OTHER PUBLICATIONS

Sheppard, N.F., et al., *Sensors and Actuators*, vol. 2, pp. 263-274, Jul. 1982.

* cited by examiner

*Primary Examiner*—Bryan Bui
(74) *Attorney, Agent, or Firm*—Hamilton, Brook, Smith & Reynolds, P.C.

(57) ABSTRACT

The condition of insulating and semiconducting dielectric materials is assessed by a sensor array that uses electric fields to interrogate the test material. The sensor has a linear array of parallel drive conductors interconnected to form a single drive electrode and sense conductors placed on each side of and parallel to a drive conductor. Subsets of the sense conductors are interconnected to form at least two sense elements sensitive to different material regions. The sense conductors may be at different distances to the drive conductors, enabling measurement sensitivity to different depths into the test material. The material condition is assessed directly from the sense element responses or after conversion to an effective material property, such as an electrical conductivity or dielectric permittivity.

28 Claims, 5 Drawing Sheets

SEGMENTED FIELD DIELECTRIC SENSOR ARRAY FOR MATERIAL CHARACTERIZATION

RELATED APPLICATION

This application claims the benefit of U.S. Provisional Application No. 60/659,266, filed on Mar. 7, 2005. The entire teachings of the above application are incorporated herein by reference.

BACKGROUND OF THE INVENTION

The technical field of this invention is that of nondestructive materials characterization, particularly quantitative, model-based characterization of surface, near-surface, and bulk material condition for flat and curved parts or components. Characterization of bulk material condition includes measurement of changes in material state, such as degradation/damage caused by damage or thermal exposure; (2) inspection for the presence of flaws or defects, such as the presence and extent of porosity or a delamination; and (3) assessment of processing-related conditions, such as cure state. Characterization of surface and near-surface conditions includes measurements of surface roughness, displacement or changes in relative position, coating thickness, temperature and coating condition. The characterization uses an electromagnetic field to interrogate a semiconducting or insulating material of interest to deduce physical, geometric, or kinematic properties.

Dielectric sensors are commonly used for material property characterization and defect detection in a material under test (MUT). The sensors respond to the absolute properties of the MUT, such as the electrical permittivity, electrical conductivity, thickness, and proximity, and changes in those properties. Factors that affect the dielectric properties include the state of cure, density, porosity, and contamination with other substances such as moisture. The property variations may be a normal part of the manufacturing process or a result of the presence of defects or damage. These defects can be created during the manufacturing process, such as improper curing or incorrect layer thickness for stratified media, or when the material is placed into service by age-related degradation processes, such as fatigue. In manufacturing, the continuing drive toward defect-free products, yield improvement and operation near the capability limits of the production system require sensing technologies for monitoring as many critical process variables as possible. In operations, service maintenance, and repair and replacement activities, the continuing push toward a retirement-for-cause philosophy from the retire-for-time approach requires reliable measurements on all fatigue-critical components in the system, even at difficult-to-access locations.

Dielectric measurements can be performed with a wide variety of devices. The simplest devices involve parallel plate capacitors where the electrodes sandwich the MUT. Often guard electrodes are used to minimize the effects of fringing electric fields at the electrode edges so that MUT is exposed to an essentially uniform electric field. The electrical terminal admittance or impedance of the device is then related to the material properties through geometric factors associated with the sensor geometry.

In many applications both sides of the MUT are not easily accessible and single-sided sensor configurations are required. A common implementation of a single-sided sensor is the interdigitated electrode structure used for chemical and moisture sensing applications (U.S. Pat. No. 4,423,371 and Sheppard et al, *Sensors and Actuators,* vol. 2, pp. 263-274, July, 1982). U.S. Pat. No. 4,814,690 further discloses the use of multiple sets of interdigitated electrodes as part of the imposed frequency-wavenumber dielectrometry approach for spatial profiling of stratified dielectric media. These devices have been effective in determining the dielectric properties of fluids. However, the determination of solid dielectric properties at multiple locations or over the surface of a test material is more difficult because of the presence of microcavities and unintentional or varying air gaps between the solid dielectric and the sensor.

SUMMARY OF THE INVENTION

Aspects of the methods described herein involve nondestructive evaluation of materials using dielectric sensor arrays for the detection and characterization of local features or condition monitoring. The sensor arrays use an electric field to interrogate a test material when the sensor is placed near the material. The field is created by driving a linear array of parallel drive conductors with a time-varying electric potential. The drive conductors are interconnected and sense conductors are placed on each side of and parallel to drive conductors. Subsets of the sense conductors are interconnected or grouped together to form at least two sense elements that are sensitive to different regions of a material. At least one of the sense elements may comprise an interdigitated structure formed with respect to the drive conductors. The at least one of the sense elements may further comprise a meandering structure formed with respect to the interdigitated structure. The responses of these sense elements are then used to assess the condition of the material. At least two of the sense elements may span different drive conductors.

Sense element conductors may be placed at different distances to the drive conductors. This allows different sense elements to respond to different segments or components of the electric field distribution. The responses to the different field components can be used individually or in combination to assess the material condition. Some of the drive conductors may be spanned by multiple sense elements so that more than one sense element can respond to the same region of the material. The sensor array may be mounted to or scanned over a test material surface. The sensor may be flexible and may comprise a foam backing to promote conformability to the material surface. The backing of the sensor array may include an expandable or pressurizable chamber such as a balloon to adjust the position and conformability of the sensor with respect to the material surface. The sensor may be attached to a rigid shuttle that approximates the shape and geometry of the test material surface. A balloon or foam backing can also be incorporated into the shuttle to keep the sensor in close proximity to the material surface. The sense element responses may be converted into effective material properties, such as an electrical conductivity, dielectric permittivity or thickness. The conversion may use a database of responses.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

This invention is directed toward the nondestructive detection and characterization of insulating or semiconducting materials using electric field based, capacitive or dielectric sensor arrays. This includes the inspection of materials for hidden objects/features and the use of models that can rapidly and accurately predict the sensor response, which allows the measured sensor responses to be converted into estimates of effective material properties. Dielectric sensor array designs permit multiple components or segments of the interrogating electric field to be sampled at more than one location on a test material using a single drive electrode.

Figure 1:
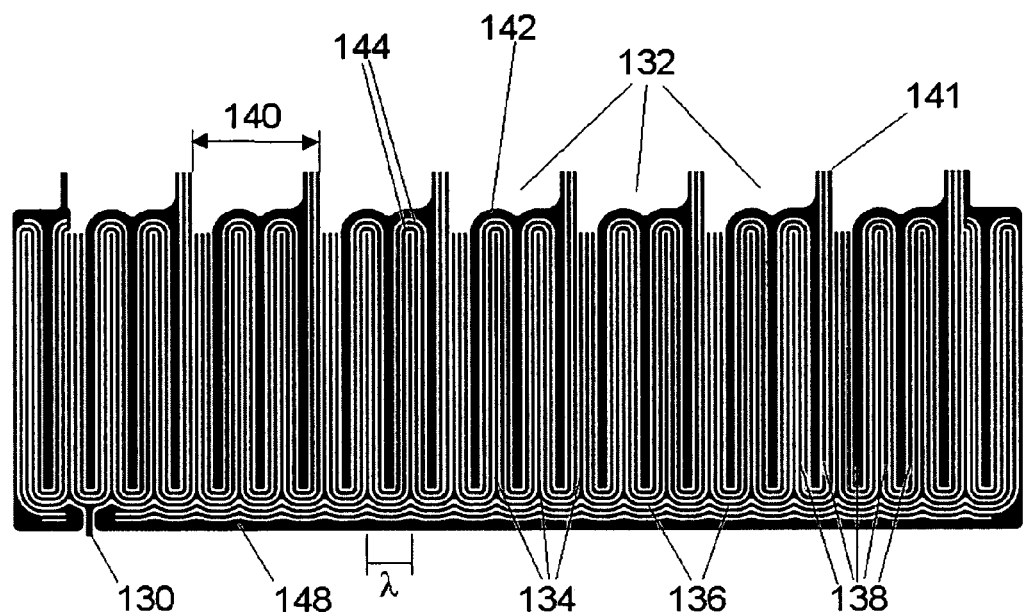
FIG. 1 shows a schematic for a dielectric sensor array.
Figure 2:
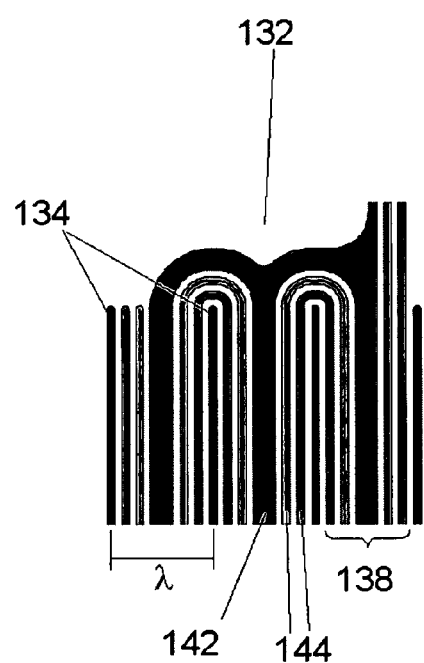
FIG. 2 shows an expanded view of a schematic for a single sense region of a dielectric sensor array.

FIG. 1 shows one embodiment of a dielectric sensor array. It shows a single drive electrode 130 for imposing a periodic electric field for interrogating a test material along with multiple sense elements 132 for sensing the material response. The drive electrode has a linear array of parallel drive conductors 134 that are interconnected at an end 136 to provide a common drive potential for each conductor. The sense elements typically include conductors 138 placed on either side of and parallel to each drive conductor, with at least some of the sense elements at different distances to the drive conductors. Several of these sense conductors are grouped together to form sensing regions 140. The sense element conductors can be grouped in different patterns, typically with the sense element conductors of each group at a common distance from the drive conductors. For example, one grouping 142 is relatively far from the drive conductors, forming a set of conductors that is interdigitated with some of the drive winding conductors. An expanded view of the electrodes for a single sense region is shown in FIG. 2. Note that this configuration is then similar to the interdigitated electrodes described in U.S. Pat. No. 4,814,690, the entire teachings of which are hereby incorporated by reference. However, in this case, the sense elements are placed into more than one group to create an array of sense elements with each group sensitive to different material regions. Furthermore, other groupings 144 have cross-connections between the sense conductors and are located closer to the drive conductors. These other groups meander between the interdigitated electrodes of the drive and the far sense element group 142. The sense conductors of the groups 144 respond to field segments or components that do not penetrate as far into the test material as the field segments that couple to the conductors of the far sense element 142. These sense elements are then sensitive to shorter spatial wavelength components of the fields, where the wavelength is determined by the periodicity of the drive electrodes λ. The use of such locally meandering and interdigitated sense electrodes allows the electrode connections 141 for each sense region to be laid out in parallel. A guard electrode 148 is placed around the structure to minimize stray coupling of the electric fields to the sense elements. It is segmented to approximately mimic the geometry within the interdigitated electrodes, which helps to prevent electrode end effects from affecting the sense element responses. When the terminal current to each sense element is measured, as opposed to the terminal voltage, this guard electrode is set to a ground potential.

There are several advantages to this array format. The single drive electrode with multiple sense electrodes effectively eliminates cross-talk between sense elements so that the response of each sense element can be measured simultaneously. This allows for faster inspections or imaging of larger areas. Another advantage of this format is that each sensing region has elements sensitive to different segments of the interrogating electric field. Similar to the approaches described in U.S. Pat. Nos. 6,380,747 and 6,486,673, the entire teachings of which are hereby incorporated by reference, this sensitivity to different segments of the field within each region allows the sensor proximity or lift-off to be treated as essentially the same for each field segment. This greatly simplifies the inversion of the measurement responses into effective material or geometric properties.

To better understand the operation of this sensor array, consider classical dielectrometry. For capacitive sensing or classical dielectrometry, the dielectric properties of a material can often be described by two parameters, the permittivity and conductivity. The permittivity is a constitutive parameter that relates the displacement current density in the material to the applied electric field, whereas the conductivity applies to the conduction current density. The dielectric properties of materials vary significantly and can provide a means for characterization of the materials and their geometric properties such as size or layer thickness.

It is often convenient to represent the complex permittivity of a material as $\in^* = \in' - j\in''$, where $\in'$ is the real part and $\in''$ is the imaginary part of the complex permittivity. The real part is the dielectric constant, or permittivity, of the material $\in' = \in$); whereas, the imaginary part ($\in'' = \sigma/\omega$ where $\sigma$ is the conductivity and $\omega$ is the angular frequency of the electric field) describes the power dissipation or loss of the material. The dielectric spectrum of a material is a representation of its complex permittivity, expressed as a function of frequency, which provides a signature of a material in a particular state. Classical dielectrometry extracts information about the state of a material construct from its dielectric spectrum.

Figure 3:
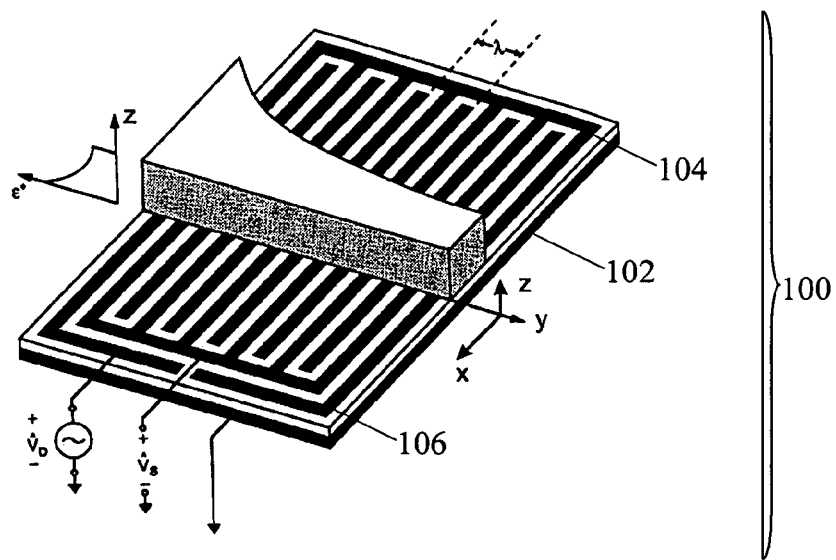
FIG. 3 is a representative single wavelength interdigitated electrode dielectrometer with spatially periodic driven and sensing electrodes that can measure dielectric properties of the adjacent material.

A representative single sided sensor geometry is shown in FIG. 3. The application of a sinusoidally time varying potential of angular frequency $\omega = 2\pi f$ results in the flow of a terminal current, whose magnitude and phase is dependent on the complex permittivity of the material. The capacitive sensor 100 has interdigitated electrodes as presented in U.S. Pat. Nos. 4,814,690, 6,380,747, 6,486,673 and 6,781,387 and in U.S. patent application Ser. No. 10/040,797, filed Jan. 7, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage $v_D$ while the other, 106, is connected to a high-impedance buffer used to measure the magnitude and phase of the floating potential $v_s$ or to a virtually grounded amplifier to measure the magnitude and phase of the terminal current. The periodicity of the electrode structure is denoted by the spatial wavelength $\lambda$. For layered media or materials having dielectric properties that vary with depth, the measured transadmittance between the drive and sense electrode, or the effective complex permittivity of the material, is a thickness and depth-weighted response of the dielectric properties of the various regions. Typical excitation frequencies range from 0.005 Hz for highly insulating materials to 10 MHz or higher for semiconducting materials.

For the interdigitated electrode dielectrometer of FIG. 3, the depth of penetration of the electric field into the material is proportional to the spatial wavelength of the periodic electrodes. The electric scalar potential in the materials above and below the sensor obeys Laplace's equation. In Cartesian coordinates with linear lossy dielectrics the potential can be written as an infinite series of sinusoidal Fourier modes of fundamental spatial wavelength $\lambda$ that decays into the medium the z direction. The periodic variation of electric potential along the surface in the y direction produces an exponentially decaying electric field that penetrates into the medium in the z direction. The depth of sensitivity is considered to be approximately ⅓ of the fundamental spatial wavelength. This implies that small wavelength sensors will primarily respond to changes of material properties near the sensor-material interface, while larger wavelength sensors respond to changes farther from the sensor interface. Thus multiple wavelength sensors can be used to measure spatial profiles of dielectric properties; the necessary information to estimate multiple unknowns with these sensors can be accomplished via different spatial wavelengths or segmented fields.

Figure 4:
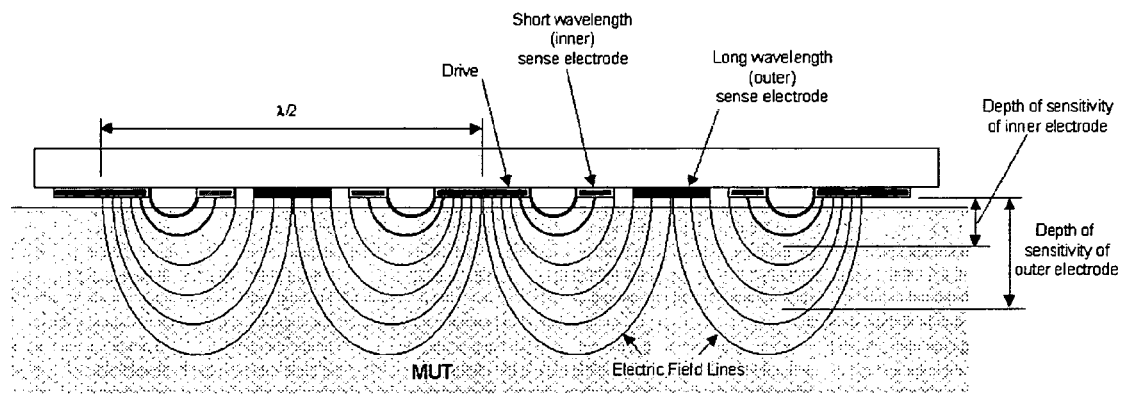
FIG. 4 shows a cross-section view of a co-located dielectric sensor with sense elements spanning the same region of the test material, ensuring that the longer and shorter wavelengths have the same average lift-off or air gap thickness.

Several types of multiple wavelength sensors have been developed. In one approach, multiple sets of interdigitated spatially periodic electrodes are laid out on a common substrate and placed in proximity to the test specimen. While this provides distinct wavelength sensors, each sensor is also sensitive to different regions of the test material. As a result, if there is a spatial variation in the thickness or dielectric properties of the test material, or if there is an air gap variation, for example, due to uneven pressure against the material or dust particles, it can be difficult to combine the measurements for meaningful property estimates. A solution is to integrate multiple sensing elements into a single sensing structure so that all of the sensing elements interrogate the same region of the material under test, as described for example in U.S. Pat. No. 6,380,747. A schematic for the electric field distribution is shown in FIG. 4, where multiple sensing electrodes are placed within each interdigitated electrode period and respond to different effective wavelength (short or long) modes of the electric field. Note that for every non-zero mode the effective wavelength is equal to the fundamental spatial wavelength divided by the mode number so that the higher order spatial modes decay faster with distance into the medium. Thus, with the multiple wavelength sense elements integrated to sense the same material region, there is sufficient information for the lift-off and dielectric constant to be measured independently. For layered materials, more sense elements can be incorporated into the geometry to sense other segments of the field distribution, which, in turn, allow the properties of more than one layer to be determined, including the air gap thickness. Circular versions of this approach have also been developed, as described for example in U.S. Pat. No. 6,486,673.

An efficient method for converting the response of the dielectric sensor into material or geometric properties is to use grid measurement methods. These methods map two known values, such as the magnitude and phase or real and imaginary parts of the sensor impedance or admittance, into the properties to be determined and provide for a real-time measurement capability. The measurement grids are two-dimensional databases that can be visualized as "grids" that relate two measured parameters to two unknowns, such as the dielectric permittivity (or electrical conductivity) and lift-off (where lift-off is defined as the proximity of the MUT to the sensor surface. For the characterization of semiconducting materials, coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for near real-time measurements of the absolute electrical properties of the material and geometric parameters of interest. The database of the sensor responses can be generated prior to the data acquisition on the part itself, so that only table lookup and interpolation operations, which are relatively fast, needs to be performed after measurement data is acquired. Furthermore, grids can be generated for the individual elements in an array so that each individual element can be lift-off compensated to provide absolute property measurements, such as the dielectric permittivity and electrical conductivity. This reduces the need for extensive calibration standards. In contrast, conventional sensing methods that use empirical correlation tables to simply relate the amplitude and/or phase of a signal to parameters or properties of interest require extensive calibrations using standards.

Figure 5:
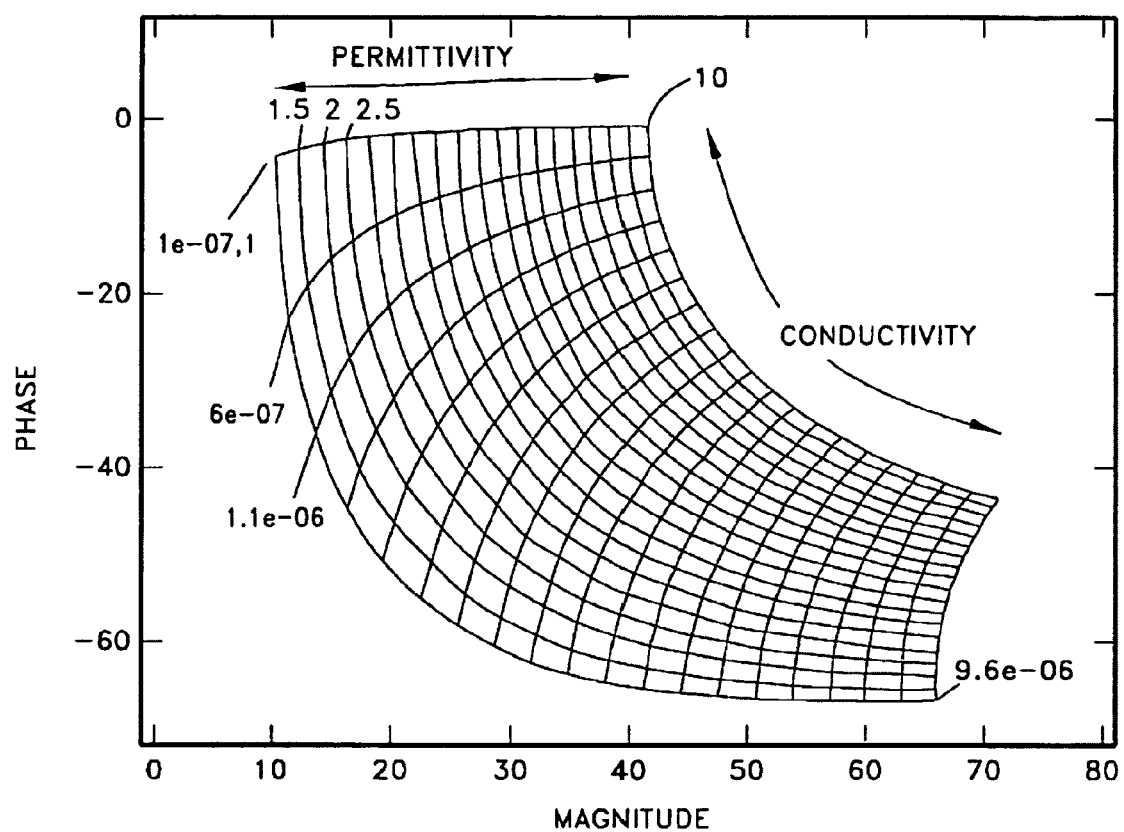
FIG. 5 shows a magnitude-phase grid for a single sense element, where the parameters being measured are permittivity and conductivity.

A representative measurement grid for a dielectric material is shown in FIG. 5 for a single sensor element. This grid can be used to estimate the permittivity and conductivity of a material assuming a value for the lift-off. If the lift-off must also be determined, then lattices can be used along with the responses from more than one sense element to determine the permittivity, conductivity, and lift-off. Note that with a significant conductivity present there is information in the phase of the signal so that each sense element response can be used to estimate two quantities independently.

Figure 6:
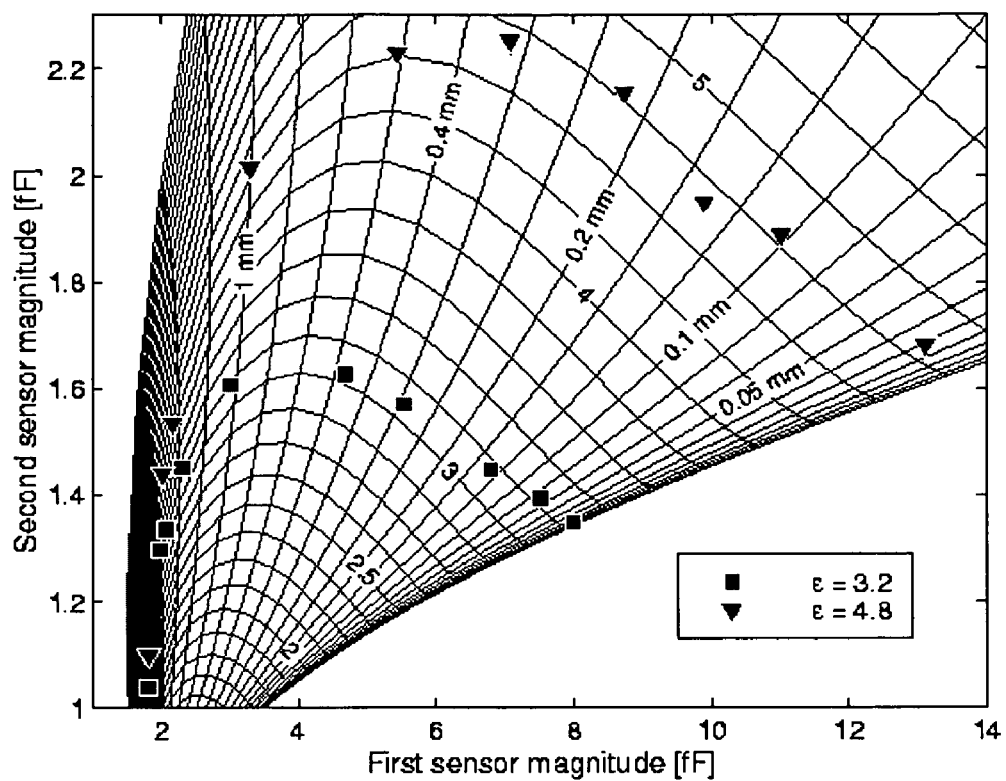
FIG. 6 shows a magnitude-magnitude grid for a two sense elements, where the parameters being measured are lift-off and dielectric permittivity.

The measurement grids can also combine information from different sense elements or sensors, as described for example in U.S. patent application Ser. No. 10/040,797, filed Jan. 7, 2002. As examples, the grid could combine magnitude responses of two sense elements, phase responses, or the magnitude of one sense element with the phase of another. As an illustration of this, consider insulating materials where the measured phase is zero. Then, the magnitude values for two separate sensors or sense elements can be used in a two-dimensional grid to estimate permittivity, thickness, lift-off, or other geometric parameters with two unknowns. An example of such a magnitude-magnitude grid is shown in FIG. 6. This shows the noncontact measurement of the permittivity of an insulating dielectric material of known thickness. The material is insulating so there is no phase information in the measurement and the magnitudes from two different wavelength-sensing elements are used to create the measurement grid. The grid illustrates the dependence of the sensed magnitudes on the dielectric constant of a material with a known thickness and the air gap between the material under test and the sensor. Sets of data points for two different materials, each 1.58-mm thick, are plotted. The flat and rigid sample materials, Lexan™ (denoted by the square symbols) and a printed circuit board (PCB) substrate (denoted by the inverted triangle symbols), were suspended above the face of the sensor to simulate noncontact measurements of the materials with various liftoffs or air gaps. For each material, the sample points approximately follow lines of constant dielectric constant.

Returning now to the array format of FIG. 1, a number of variations can also be considered. The sense elements can be grouped in a variety of ways. Non-overlapping sense elements can be formed by making interdigitated sense elements and any meandering sense elements span the same drive conductors. Overlapping sense elements can be formed by making at least one of the sense elements span different conductors than another sense element. Preferably, this is done in a spatially periodic fashion so that the array of sense elements provide a similar response when placed at a uniform distance from a homogeneous test material. This type of grouping of sense elements has been described for example in U.S. Pat. No. 6,727,691 for periodic magnetic field sensor arrays, the entire teachings of which are hereby incorporated by reference. Of course the dimensions of the sensor array geometry and the placement of the sense elements can be adjusted to improve sensitivity for a specific application. This includes varying the spacing between the drive conductor segments and one or more of the parallel conducting segments used for sensing the response to the test material.

Some of the motivation for the use of multiple sensing elements is to increase the spatial resolution of the material being characterized without loss of coverage, to add additional information for use in the estimation of multiple unknown material properties, and to cover large inspection areas in a faster time. When being used to inspect a material or monitor material condition, the sensor arrays can be mounted to the material surface or scanned over the material surface. One example application is the mounting of the sensor array to a dielectric material for fatigue monitoring. Another is the mounting onto a flexible substrate or support to permit conformability to test material surfaces having a curved geometry when scanning the sensor array over the surface. The sensor can be mounted onto rigid supports that approximate the shape of the test material, with an intermediate layer such as a foam to enhance conformability, as described for example in U.S. Pat. No. 6,781,387 and in U.S. patent application Ser. No. 10/650,486, filed Aug. 28, 2003, the entire teachings of which are hereby incorporated by reference. The support can include an expandable or pressurizable element, such as a balloon, as well as a rigid shuttle to facilitate placement of the sensor into confined areas. The shuttle shape may approximate the shape of the test material surface being monitored or scanned.

Figure 7:
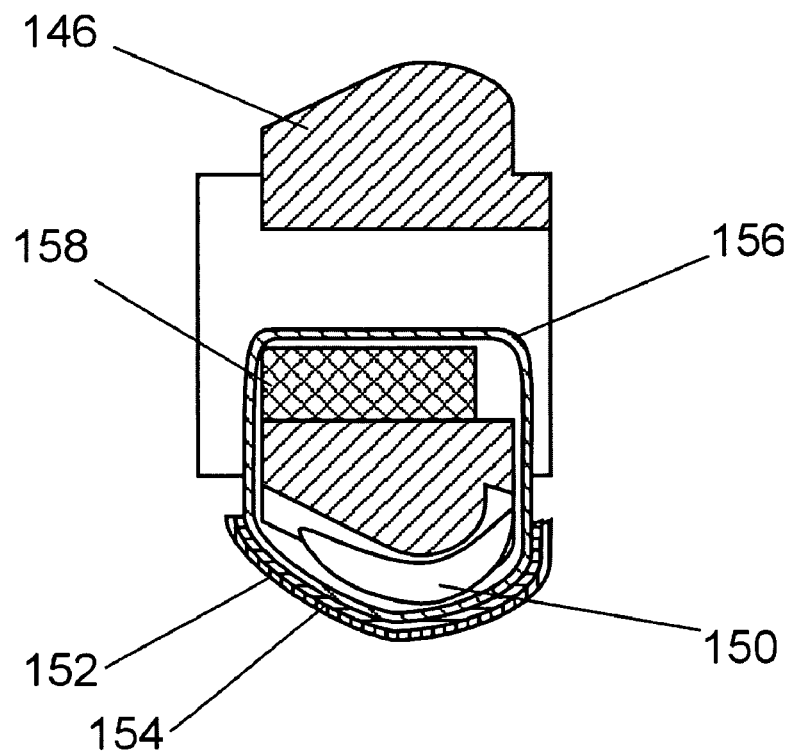
FIG. 7 shows a cross-sectional view of a shuttle probe containing a rigid support and a balloon.

An example probe shuttle for the inspection of concave openings or holes is shown in FIG. 7. A flexible dielectric sensor array 154 is attached to a flexible ring 156 that surrounds a balloon 150, part of the solid portion of the probe shuttle 146, and a foam spring 158. The balloon 150 presses the sensor 154 against the test material with a nominally uniform force during the inspection. The flexible ring 156 transmits the motion from the foam spring 158 to the sensor 154, which allows the foam spring to return the sensor 154 to its initial position and deflate the balloon 150 upon completion of an inspection. An outer protective layer 152 is also used to protect the sensor 154 and balloon 150 from wear and shearing forces. Preferably, the flexible material for the sensor, the surrounding ring, and the outer protective wear material is Kapton™. In operation, the shuttle is slid along into the test article with the balloon 150 deflated. Once inside the test article, the balloon 150 is inflated. This, in turn, presses the sensor 154 against the surface of the test material for the inspection. After completion of the inspection, releasing the pressure on the balloon 150 allows the foam spring 158 inside the shuttle 146 to deflate the balloon 150 back to its original form. Any fluid (gas or liquid) can be used to inflate and deflate the balloons. Typically, air or water is used.

Figure 8:
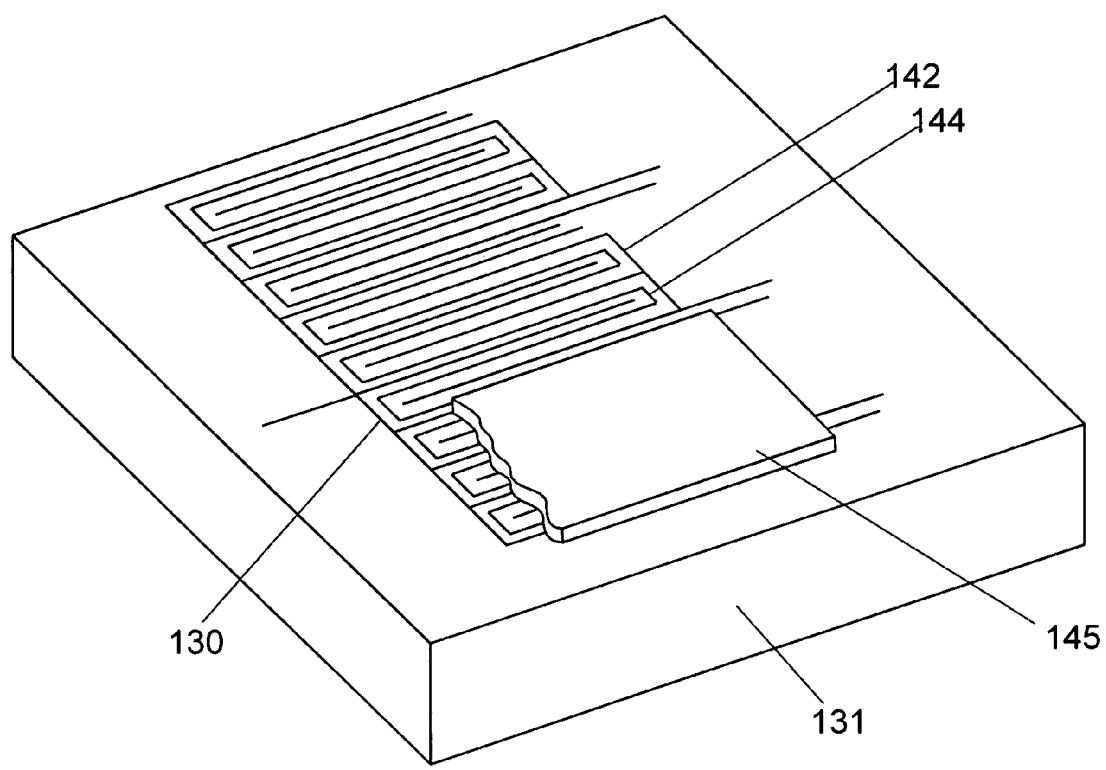
FIG. 8 shows a schematic for a dielectric sensor array mounted on a test material surface, with one sense element region covered by an environmentally sensitive layer.

In some situations, such as with the monitoring of corrosion protection coatings, it is desirable to monitor the condition of the test material as well as the environmental conditions in the vicinity of the test material. For the case of a corrosion protection coating, the test material is the coating and the sensor may be mounted on top of the coating or embedded inside or under the coating, proximate to the material being protected by the coating. Then, the condition of the protective coating as well as the exposure to potentially harmful conditions can be monitored. As an example, consider the mounted sensor array shown in FIG. 8. In this case the sensor array has three sense regions and is mounted onto a test material 131. In this simplified schematic, the conductors are represented with lines and the additional conductors, such as the guard electrodes that are typically placed at the ends of the array, have not been added. While the dielectric sensor may itself be sensitive to the environmental conditions, an additional diagnostic layer 145 may be added to one or more sense element regions to enhance the sensitivity of the dielectric sensor to the environmental factor. The dielectric permittivity, electrical conductivity, or even layer thickness may change as a result of the exposure to this environmental factor and dielectric sensor is able to monitor these changes. For example, Kapton™ is known to be hydrophilic and the dielectric permittivity changes significantly with relative humidity. For the corrosion example, the diagnostic layer may provide sensitivity to corrosion by-products. Furthermore, for these mounted sensor arrays, one or more sense elements may be located in areas where the material condition is likely to change due to usage, damage, or environmental factors while another sense element is placed in an area where the material condition is unlikely to change. As examples, usage can be stress or temperature, damage can be cracks, porosity, or delamination, and environmental factors can include moisture, humidity, or contamination.

While the inventions have been particularly shown and described with reference to preferred embodiments thereof, it will be understood to those skilled in the art that various changes in form and details may be made therein without departing from the spirit and scope of the invention as defined by the appended claims.

What is claimed is:

1. A method for characterizing a material comprising
disposing a dielectric sensor proximate to a test material surface, the sensor having a linear array of parallel drive conductors to impose an electric field in a test material when driven by an electric voltage, sense conductors of a sense element placed on each side of and parallel to a drive conductor, and subsets of the sense conductors interconnected in at least two respective sense elements over respective adjacent continuous surface regions;

measuring a response of each sense element; and providing a material condition assessed from the response.

2. The method as claimed in claim 1 wherein the a sense element comprises sense conductors at different distances to the drive conductors.

3. The method as claimed in claim 2 wherein the responses from the sense conductors at different distances to the drive conductors are combined and used to assess the material condition.

4. The method as claimed in claim 1 wherein the sense elements span different drive conductors.

5. The method as claimed in claim 1 wherein some of the drive conductors are adjacent to multiple sense elements.

6. The method as claimed in claim 1 wherein the sensor is mounted to the surface.

7. The method as claimed in claim 1 wherein the sensor is scanned over the surface.

8. The method as claimed in claim 1 further comprising the sensor is flexible and has a foam backing.

9. The method as claimed in claim 1 further comprising the sensor is flexible and mounted onto a balloon.

10. The method as claimed in claim 9 further comprising the sensor and balloon are mounted on a rigid shuttle that approximates the shape of a test material surface.

11. The method as claimed in claim 1 further comprising convening the sense element responses into an effective material property.

12. The method as claimed in claim 11 wherein the conversion uses a database of responses.

13. The method as claimed in claim 11 wherein the material property is electrical conductivity.

14. The method as claimed in claim 11 wherein the material property is dielectric permittivity.

15. The method as claimed in claim 1 wherein a diagnostic layer is added to at least one region covering at least one sense element, the diagnostic layer providing sensitivity to an environmental condition.

16. The method as claimed in claim 1 wherein at least one of the sense elements comprises an interdigitated structure formed with respect to the drive conductors.

17. The method as claimed in claim 16 wherein the at least one of the sense elements further comprises a meandering structure formed with respect to the interdigitated structure.

18. A dielectric sensor comprising a linear array of parallel drive conductors, the drive conductors imposing an electric field in a test material when driven by an electric voltage; and sense conductors of respective sense elements placed on each side of and parallel to a drive conductor, subsets of the sense conductors being interconnected in at least two sense elements over respective adjacent continuous surface regions.

19. The dielectric sensor of claim 18 wherein a sense element comprises an interdigitated structure formed with respect to the drive conductors.

20. The dielectric sensor of claim 19 wherein the at least one of the sense elements further comprises a meandering structure formed with respect to the interdigitated structure.

21. The dielectric sensor of claim 18 wherein the at least two sense elements comprise sense conductors at different distances to the drive conductors.

22. The dielectric sensor of claim 21 wherein the responses from the sense conductors at different distances to the drive conductors are combined and used to assess the material condition.

23. The dielectric sensor as claimed in claim 18 wherein a diagnostic layer is added to at least one region covering at least one sense element, the diagnostic layer having at least one material property that varies with exposure to the environmental condition.

24. The dielectric sensor as claimed in claim 23 wherein the environmental condition is humidity.

25. The dielectric sensor as claimed in claim 23 wherein the environmental condition is contamination.

26. A method for characterizing a material comprising:

disposing a dielectric sensor proximate to a test material surface, the sensor having a linear array of parallel drive conductors to impose an electric field in a test material when driven by an electric voltage, sense conductors placed on either side of and parallel to a drive conductor, and subsets of the sense conductors interconnected to form at least two sense elements over respective adjacent surface regions;

adding a diagnostic layer to at least one region covering at least one sense element, the diagnostic layer providing sensitivity to an environmental condition measuring a response of each sense elements; and providing a material condition assessed from the response.

27. The method as claimed in claim 26 wherein the environmental condition is humidity.

28. The method as claimed in claim 26 wherein the environmental condition is contamination.

* * * * *

UNITED STATES PATENT AND TRADEMARK OFFICE
CERTIFICATE OF CORRECTION

| | | |
|---|---|---|
| PATENT NO. | : 7,280,940 B2 | Page 1 of 1 |
| APPLICATION NO. | : 11/371315 | |
| DATED | : October 9, 2007 | |
| INVENTOR(S) | : Neil J. Goldfine et al. | |

It is certified that error appears in the above-identified patent and that said Letters Patent is hereby corrected as shown below:

Column 9

In Claim 11, line 33, please delete "convening" and insert -- converting --

Signed and Sealed this

First Day of April, 2008

JON W. DUDAS
*Director of the United States Patent and Trademark Office*